US010073950B2

(12) United States Patent
Wang et al.

(10) Patent No.: US 10,073,950 B2
(45) Date of Patent: Sep. 11, 2018

(54) TELEPRESENCE ROBOT WITH A CAMERA BOOM (71) Applicant: INTOUCH TECHNOLOGIES, INC., Goleta, CA (US)

(72) Inventors: Yulun Wang, Goleta, CA (US); Charles S. Jordan, Mill Spring, NC (US); Kevin Hanrahan, Santa Barbara, CA (US); Daniel Sanchez, Summerland, CA (US); Marco Pinter, Goleta, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

(21) Appl. No.: 14/594,729

(22) Filed: Jan. 12, 2015

(65) Prior Publication Data
US 2015/0127156 A1 May 7, 2015

Related U.S. Application Data (63) Continuation of application No. 12/210,102, filed on Oct. 21, 2008, now Pat. No. 8,996,165.

(51) Int. Cl.
A61B 5/00 (2006.01)
H04N 7/15 (2006.01)
(Continued)

(52) U.S. Cl.
CPC ........ G06F 19/3418 (2013.01); A61B 5/0013 (2013.01); A61B 5/7445 (2013.01);
(Continued)

(58) Field of Classification Search
CPC .... G06F 19/3418; G06F 19/3425; B25J 5/00; B25J 5/007; B25J 11/009; B25J 9/1689; H04N 7/15; A61B 5/0002; A61B 5/0013; A61B 5/0015–5/0022; A61B 5/7465; A61B 5/7445
See application file for complete search history.

(56) References Cited

U.S. PATENT DOCUMENTS 4,553,309 A 11/1985 Hess et al.
5,617,539 A 4/1997 Ludwig et al.
(Continued)

OTHER PUBLICATIONS

Klapan et al., "Tele-3-dimensional computer-assisted functional endoscopic sinus surgery: New dimension in the surgery of the nose and paranasal sinuses" Dec. 2002, Otolaryngology-Head and Neck Surgery, vol. 127 No. 6, pp. 549-557.*
(Continued)

Primary Examiner — Spencer D Patton (57) ABSTRACT

A remote controlled robot with a head that supports a monitor and is coupled to a mobile platform. The mobile robot also includes an auxiliary camera coupled to the mobile platform by a boom. The mobile robot is controlled by a remote control station. By way of example, the robot can be remotely moved about an operating room. The auxiliary camera extends from the boom so that it provides a relatively close view of a patient or other item in the room. An assistant in the operating room may move the boom and the camera. The boom may be connected to a robot head that can be remotely moved by the remote control station.

14 Claims, 5 Drawing Sheets (51) Int. Cl.
*B25J 5/00* (2006.01)
*G06F 19/00* (2018.01)
*G16H 40/67* (2018.01)

(52) U.S. Cl.
CPC .............. *A61B 5/7465* (2013.01); *B25J 5/00* (2013.01); *G16H 40/67* (2018.01); *H04N 7/15* (2013.01)

(56) References Cited

U.S. PATENT DOCUMENTS

| | | | |
|---|---|---|---|
| 5,867,494 A | 2/1999 | Krishnaswamy et al. | |
| 6,292,713 B1 * | 9/2001 | Jouppi | G06F 3/011 |
| | | | 345/629 |
| 6,292,714 B1 | 9/2001 | Okabayashi | |
| 6,314,631 B1 | 11/2001 | Pryor | |
| 6,317,953 B1 | 11/2001 | Pryor | |
| 6,373,855 B1 | 4/2002 | Downing et al. | |
| 6,411,055 B1 | 6/2002 | Fujita et al. | |
| 6,667,592 B2 | 12/2003 | Jacobs et al. | |
| 6,674,259 B1 | 1/2004 | Norman et al. | |
| 6,893,267 B1 | 5/2005 | Yueh | |
| 6,990,112 B1 | 1/2006 | Brent et al. | |
| 7,222,000 B2 | 5/2007 | Wang et al. | |
| 7,467,211 B1 | 12/2008 | Herman et al. | |
| 7,483,867 B2 | 1/2009 | Ansari et al. | |
| 7,631,833 B1 | 12/2009 | Ghaleb et al. | |
| 7,657,560 B1 | 2/2010 | DiRienzo | |
| 7,703,113 B2 | 4/2010 | Dawson | |
| 7,737,993 B2 | 6/2010 | Kaasila et al. | |
| 8,126,960 B2 | 2/2012 | Obradovich et al. | |
| 8,320,534 B2 | 11/2012 | Kim et al. | |
| 8,374,171 B2 | 2/2013 | Cho et al. | |
| 8,400,491 B1 | 3/2013 | Panpaliya et al. | |
| 8,401,275 B2 | 3/2013 | Wang et al. | |
| 8,423,284 B2 | 4/2013 | O'Shea | |
| 8,451,731 B1 | 5/2013 | Lee et al. | |
| 8,515,577 B2 | 8/2013 | Wang et al. | |
| 8,610,786 B2 | 12/2013 | Ortiz | |
| 8,612,051 B2 | 12/2013 | Norman et al. | |
| 8,639,797 B1 | 1/2014 | Pan et al. | |
| 8,670,017 B2 | 3/2014 | Stuart et al. | |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 8,996,165 B2 | 3/2015 | Wang et al. | |
| 2002/0015296 A1 * | 2/2002 | Howell | E04B 9/006 |
| | | | 362/11 |
| 2002/0109775 A1 | 8/2002 | White et al. | |
| 2002/0128985 A1 | 9/2002 | Greenwald | |
| 2003/0135097 A1 | 7/2003 | Wiederhold et al. | |
| 2003/0195662 A1 | 10/2003 | Wang et al. | |
| 2004/0143421 A1 * | 7/2004 | Wang | B25J 5/007 |
| | | | 702/188 |
| 2004/0218099 A1 | 11/2004 | Washington | |
| 2004/0260790 A1 | 12/2004 | Balloni et al. | |
| 2005/0052527 A1 * | 3/2005 | Remy | H04N 7/185 |
| | | | 348/14.08 |
| 2005/0073575 A1 | 4/2005 | Thacher et al. | |
| 2005/0149364 A1 | 7/2005 | Ombrellaro | |
| 2006/0056655 A1 | 3/2006 | Wen et al. | |
| 2006/0056837 A1 | 3/2006 | Vapaakoski | |
| 2006/0066609 A1 | 3/2006 | Iodice et al. | |
| 2006/0071797 A1 | 4/2006 | Rosenfeld et al. | |
| 2006/0161303 A1 * | 7/2006 | Wang | B25J 9/1689 |
| | | | 700/259 |
| 2007/0093279 A1 | 4/2007 | Janik | |
| 2007/0116152 A1 | 5/2007 | Thesling | |
| 2007/0170886 A1 | 7/2007 | Plishner | |
| 2007/0226949 A1 | 10/2007 | Hahm et al. | |
| 2007/0263079 A1 * | 11/2007 | Graham | H04N 7/142 |
| | | | 348/14.08 |
| 2007/0290040 A1 | 12/2007 | Wurman et al. | |
| 2008/0051985 A1 | 2/2008 | D'Andrea et al. | |
| 2008/0091340 A1 | 4/2008 | Milstein et al. | |
| 2008/0161969 A1 | 7/2008 | Lee et al. | |
| 2008/0232763 A1 | 9/2008 | Brady | |
| 2008/0263628 A1 | 10/2008 | Norman et al. | |
| 2008/0267069 A1 | 10/2008 | Thielman et al. | |
| 2009/0102919 A1 | 4/2009 | Zamierowski et al. | |
| 2010/0066804 A1 | 3/2010 | Shoemake et al. | |
| 2010/0171826 A1 | 7/2010 | Hamilton et al. | |
| 2010/0278086 A1 | 11/2010 | Pochiraju et al. | |
| 2010/0301679 A1 | 12/2010 | Murray et al. | |
| 2011/0022705 A1 | 1/2011 | Yellamraju et al. | |
| 2011/0071675 A1 | 3/2011 | Wells et al. | |
| 2011/0072114 A1 | 3/2011 | Hoffert et al. | |
| 2011/0193949 A1 | 8/2011 | Nambakam et al. | |
| 2011/0280551 A1 | 11/2011 | Sammon | |
| 2012/0059946 A1 | 3/2012 | Wang | |
| 2012/0113856 A1 | 5/2012 | Krishnaswamy | |
| 2012/0203731 A1 | 8/2012 | Nelson et al. | |
| 2012/0291809 A1 | 11/2012 | Kuhe et al. | |
| 2013/0250938 A1 | 9/2013 | Anandakumar et al. | |
| 2014/0047022 A1 | 2/2014 | Chan et al. | |
| 2014/0085543 A1 | 3/2014 | Hartley et al. | |
| 2014/0135990 A1 | 5/2014 | Stuart et al. | |
| 2014/0139616 A1 | 5/2014 | Pinter et al. | |
| 2014/0155755 A1 | 6/2014 | Pinter et al. | |

OTHER PUBLICATIONS

Screenshot Showing Google Date for Lemaire Telehealth Manual, Screenshot Retrieved on Dec. 18, 2014, 1 page.

Nomadic Technologies, Inc., "Nomad Scout Language Reference Manual", Software Version: 2.7, Part No. DOC00002, Jul. 12, 1999, 47 pages.

Fulbright et al., "SWAMI: An Autonomous Mobile Robot for Inspection of Nuclear Waste of Storage Facilities", Autonomous Robots, vol. 2, 1995, pp. 225-235.

* cited by examiner

TELEPRESENCE ROBOT WITH A CAMERA BOOM

BACKGROUND OF THE INVENTION

1. Field of the Invention

The subject matter disclosed generally relates to the field of tele-presence.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile robot introduced by InTouch Technologies, Inc., the assignee of this application, under the trademark RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

The InTouch robot system can be used by doctors to remotely view and diagnose patients. For example, the robot can be used in an operating room so the remote operator can provide assistance in a procedure. Some operating rooms include monitors and/or cameras that are mounted on booms. The cameras may provide images to the remote viewer. The cameras are located relatively far from the operating table or provide an undesirable vantage point such that the images may not be of a satisfactory quality for the remote user. For example, the remote user may want a higher quality image of a wound or surgical site of the patient. Additionally, there are operating rooms that do not have boom mounted cameras. It would be desirable to provide a remote camera function for such rooms in a cost effective manner.

BRIEF SUMMARY OF THE INVENTION

A remote controlled robot with a head that supports a monitor and is coupled to a mobile platform. The mobile robot also includes an auxiliary camera coupled to the mobile platform by a boom.

DETAILED DESCRIPTION

Disclosed is a remote controlled robot with a head that supports a monitor and is coupled to a mobile platform. The mobile robot also includes an auxiliary camera coupled to the mobile platform by a boom. The mobile robot is controlled by a remote control station. By way of example, the robot can be remotely moved about an operating room. The auxiliary camera extends from the boom so that it provides a relatively close view of a patient or other item in the room. An assistant in the operating room may move the boom and the camera. The boom may be connected to a robot head that can be remotely moved by the remote control station by moving a robot head. Alternatively, the boom may be connected to the body of the robot and remotely moved by moving the robot.

Figure 1:
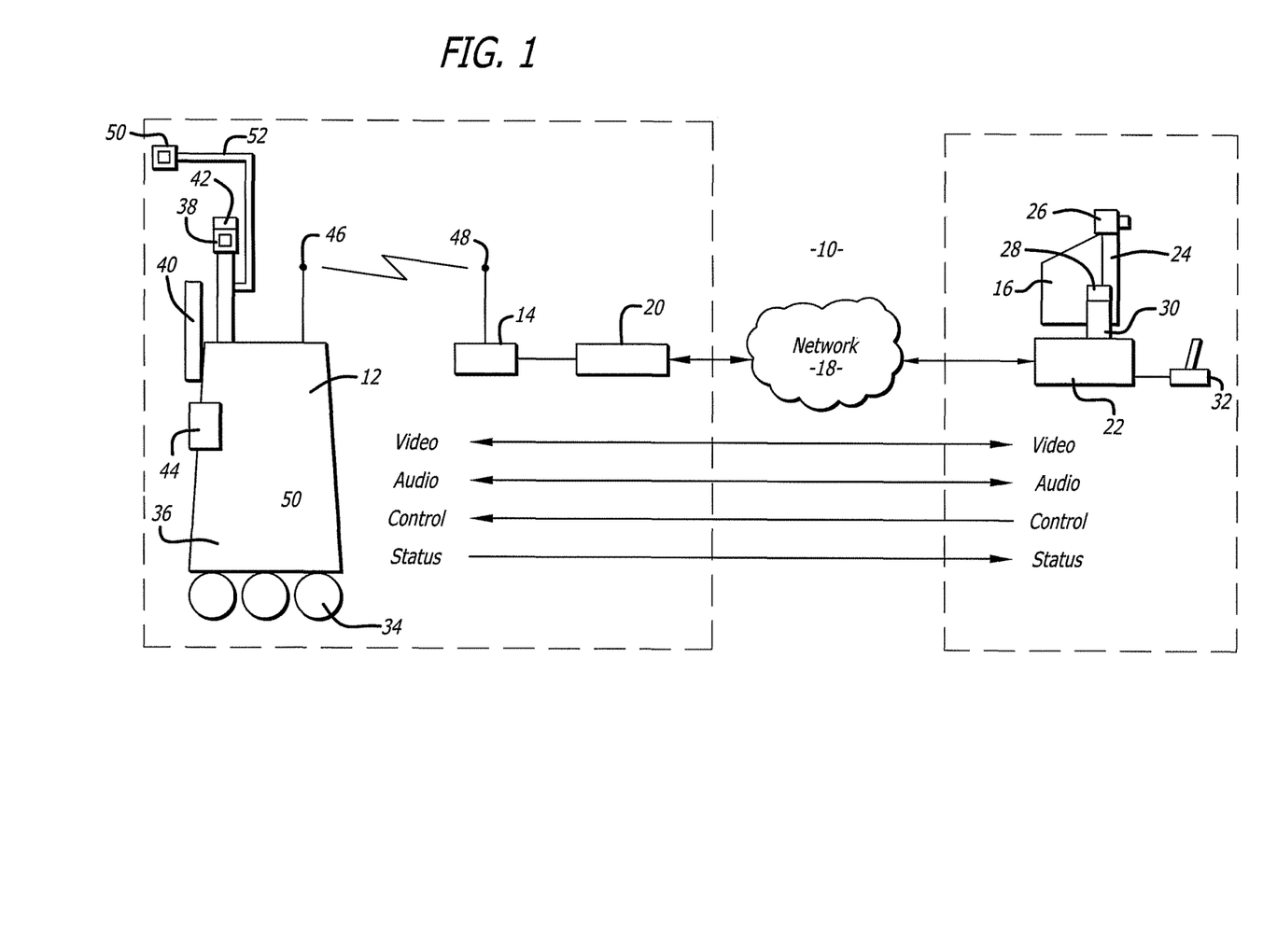
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 is a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a subject such as a patient. Likewise, the robot monitor 40 is coupled to the remote camera 26 so that the patient can view the user. The microphones 28 and 42, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The robot 12 includes an auxiliary camera 50 that extends from a boom 52. The boom 52 may have one or more passive joints such as slip, spring or ratchet joints. The camera 50 may also have a passive and/or active movement mechanism. This allows someone to manually move the position of the camera 50 relative to the robot 12. The auxiliary camera 50 can be attached to the electrical system of the robot 12 so that images captured by the camera 50 are transmitted to the remote control station 16 via the robot 12.

Alternatively, the camera 50 may directly wirelessly transmit the video to the robot 12 for further transmission to the base station 14.

The camera 50 can be connected to the boom 52 with a quick release mechanism (not shown). The quick release mechanism allows the camera 50 to be readily detached from the boom 52. The camera 50 may a battery and a wireless transmitter that allows for hand held usage. The wireless transmitter may transmit images to the robot 12 for further transmission to the remote station 14.

Figure 2:
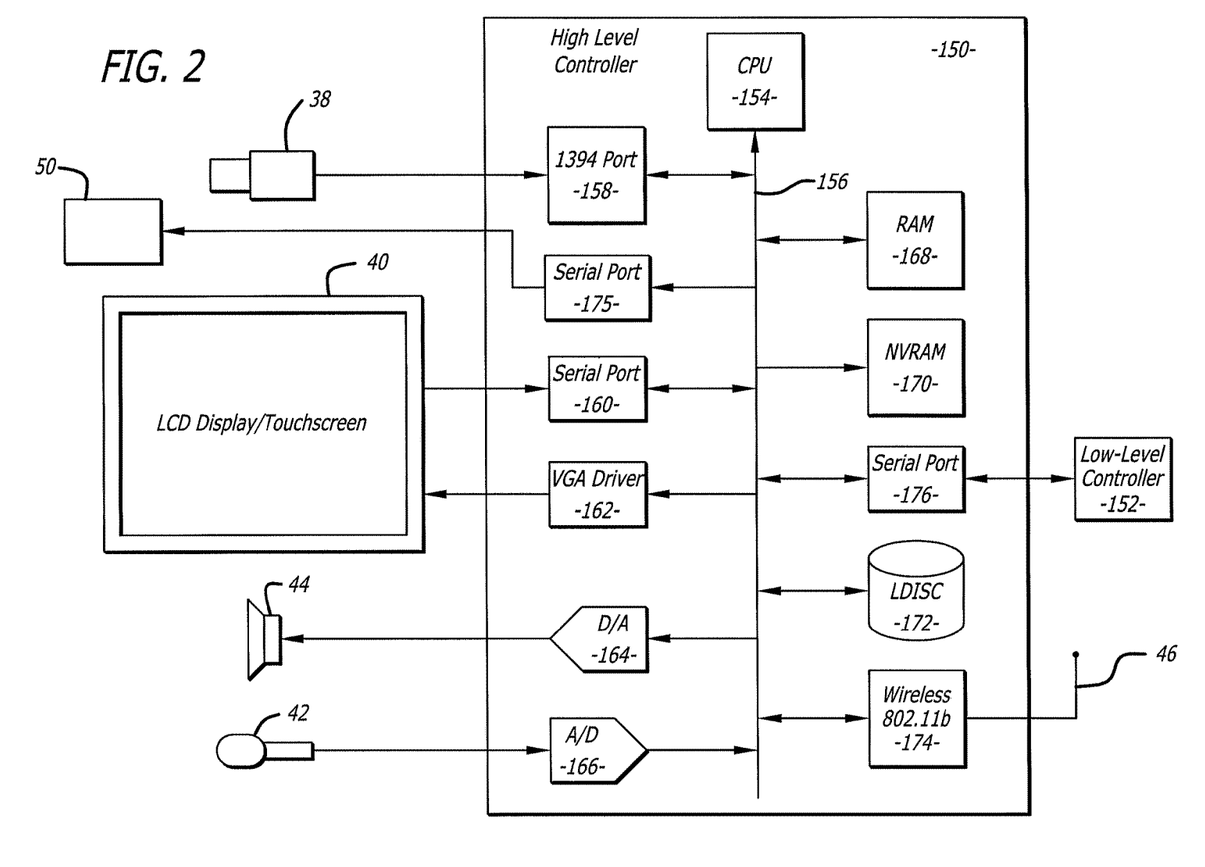
FIG. 2 is a schematic of an electrical system of the robot.

FIG. 2 shows an embodiment of a robot 12. Each robot 12 may include a high level control system 150 and a low level control system 152. The high level control system 150 may include a processor 154 that is connected to a bus 156. The bus 156 is coupled to the camera 38 by an input/output (I/O) port 158. The monitor 40 is coupled to the bus 156 by a serial output port 160 and a VGA driver 162. The monitor 40 may include a touchscreen function that allows a user to enter input by touching the monitor screen.

The speaker 44 is coupled to the bus 156 by a digital to analog converter 164. The microphone 42 is coupled to the bus 156 by an analog to digital converter 166. The high level controller 150 may also contain random access memory (RAM) device 168, a non-volatile RAM device 170 and a mass storage device 172 that are all coupled to the bus 156. The mass storage device 172 may contain medical files of the patient that can be accessed by the user at the remote control station 16. For example, the mass storage device 172 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 174. By way of example, the transceiver 174 may transmit and receive information in accordance with IEEE 802.11b.

The auxiliary camera 50 may be coupled to the bus 156 by a serial output port 175. The serial port 175 may include a Universal Asynchronous Receiver/Transmitter ("UART") interface.

The controller 154 may operate with a LINUX OS operating system. The controller 154 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 150 operates to control communication between the robot 12 and the remote control station 16.

The remote control station 16 may include a computer that is similar to the high level controller 150. The computer would have a processor, memory, I/O, software, firmware, etc. for generating, transmitting, receiving and processing information.

The high level controller 150 may be coupled to the low level control circuit 152 by serial port 176. The low level control 152 runs software routines that mechanically actuate the robot 12. For example, the low level control 152 provides instructions to actuate the movement platform to move the robot 12. The low level control 152 may receive movement instructions from the high level control 150. The movement instructions may be received as movement commands from the remote control station or another robot. Although two controllers are shown, it is to be understood that each robot 12 may have one controller, or more than two controllers, controlling the high and low level functions.

Figure 3:
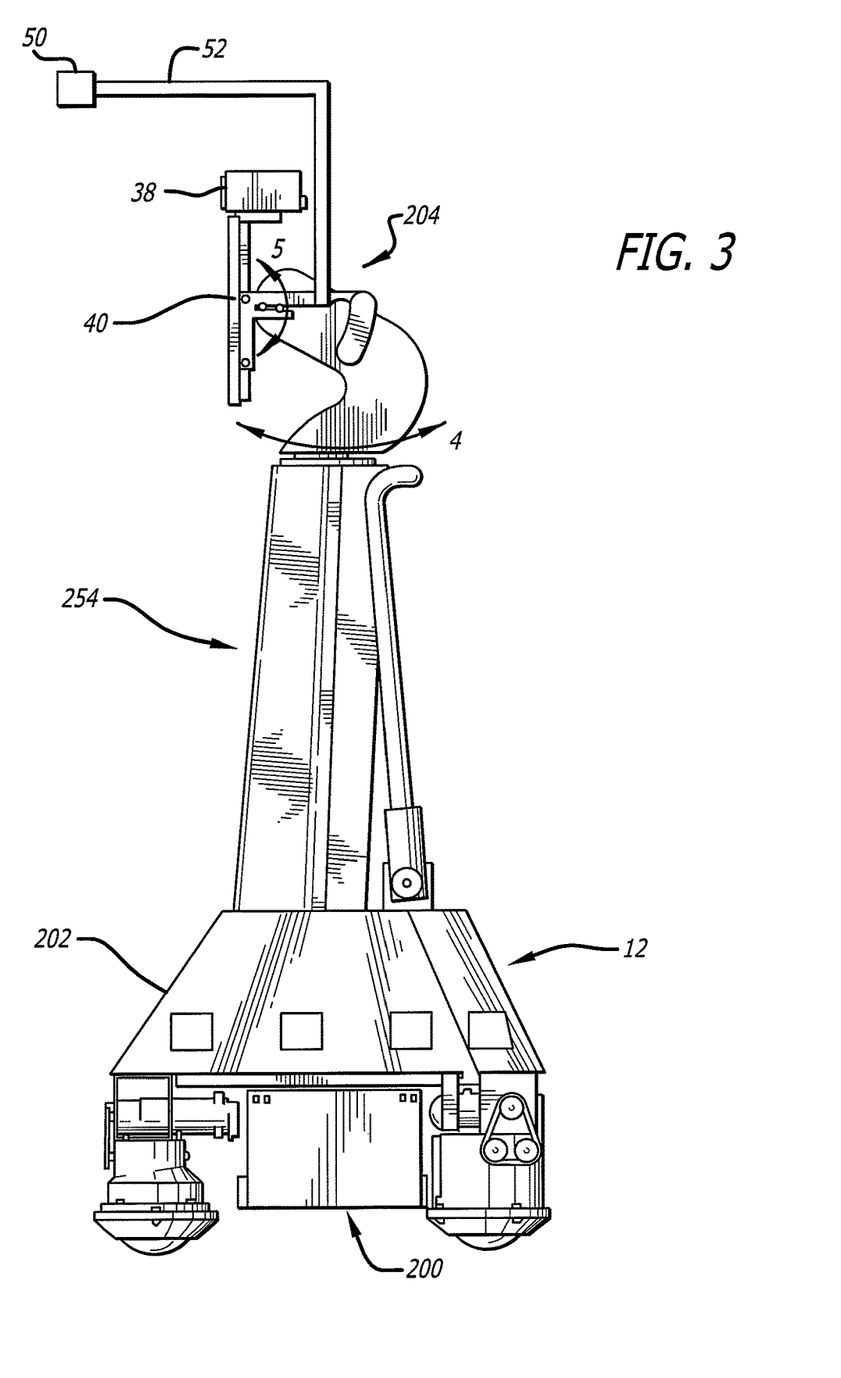
FIG. 3 is an illustration of a robot.

FIG. 3 shows an embodiment of the robot 12. The robot 12 may include a holonomic platform 200 that is attached to a robot housing 202. The holonomic platform 200 provides three degrees of freedom to allow the robot 12 to move in any direction.

The robot 12 may have a head 204 that supports the camera 38, the monitor 40 and boom 52. The head 204 may have two degrees of freedom so that the camera 38, monitor 40 and auxiliary camera 50 can together be swiveled and pivoted as indicated by the arrows. The system may be the same or similar to a robotic system provided by the assignee InTouch-Health, Inc. of Santa Barbara, Calif. under the name RP-7. The system may also be the same or similar to the system disclosed in U.S. Pat. No. 6,925,357 issued Aug. 2, 2005, which is hereby incorporated by reference.

Figure 4:
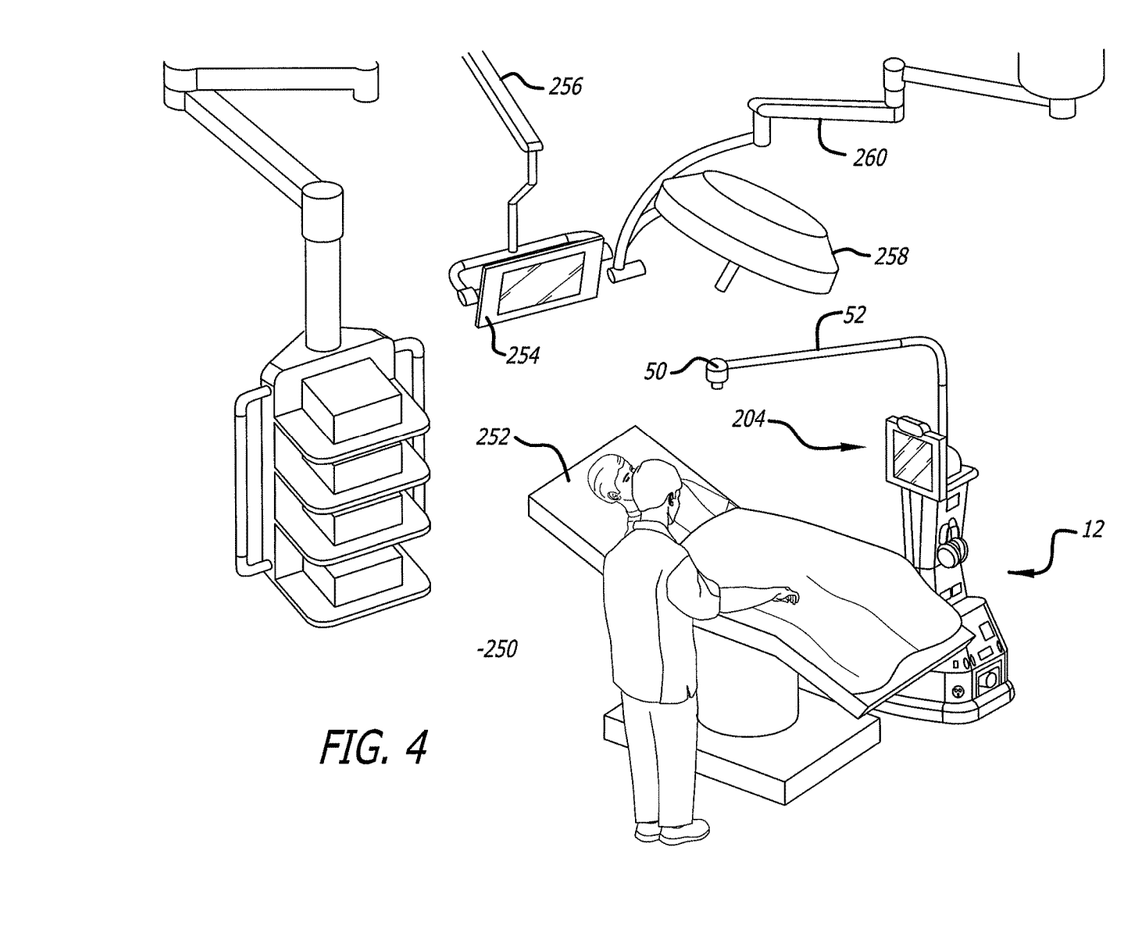
FIG. 4 is an illustration of a mobile robot in an operating room.

As shown in FIG. 4 the robot 12 can be maneuvered about an operating room 250 that has an operating table 252. The room 250 may also have a monitor 254 located at the end of a boom 256 and a lamp 258 supported by boom 260.

The robot 12 can be moved by the operator at the remote station (not shown) so that the auxiliary camera 50 is located above the operating table 252. A person in the operating room may manually adjust the robot boom 52 to obtain a desired view through the camera 50. The remote operator may also move the auxiliary camera 50 by actuating the robot head 204 in the pan and/or tilt degrees of freedom. Mounting the auxiliary camera on the end of the boom 52 allows the camera 50 to take pictures/video of a patient located on the table 252 from a preferred vantage point.

Figure 5:
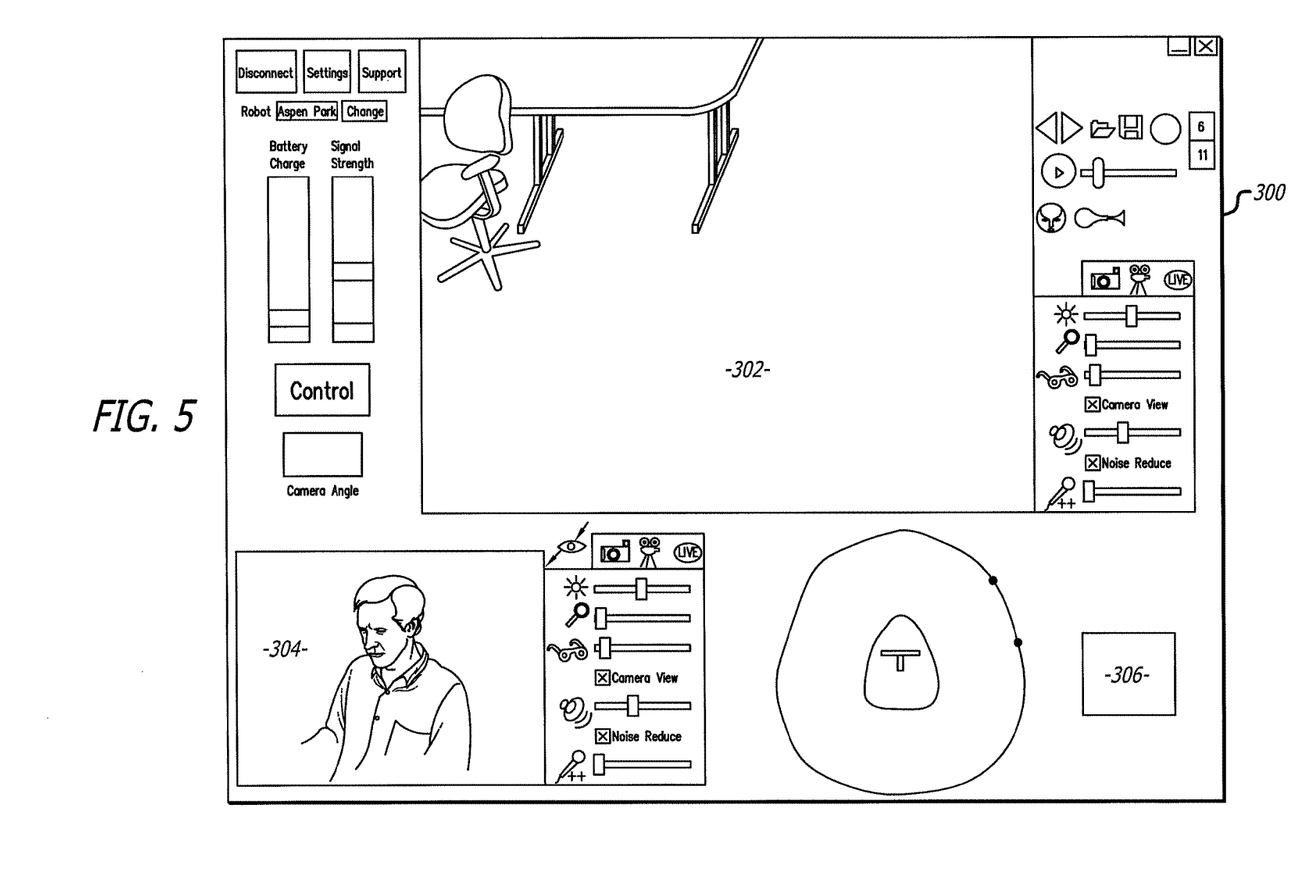
FIG. 5 is a graphical user interface of a remote station.

FIG. 5 shows a display user interface ("DUI") 300 that can be displayed at the remote station 16. The DUI 300 may include a robot view field 302 that displays a video image provided by the camera of the robot. The DUI 300 may also include a station view field 304 that displays a video image provided by the camera of the remote station 16. The DUI 300 may also have an auxiliary camera field 306 that displays the picture/video provided by the auxiliary camera of the robot. The DUI may have a graphical button (not shown) that can be selected so the auxiliary camera image is displayed in field 302. When the auxiliary image is displayed in field 302 the robot may operate in a mode that minimizes vibration and other disturbances that may cause unwanted movement of the camera 50. The DUI 300 may be part of an application program stored and operated by the computer 22 of the remote station 16. The display user interface and the various features and functions provided by the interface may be the same or similar to the DUI provided by the RP-7 system.

The robot 12 can be maneuvered through a site such as an operating room by manipulating the input device 32 at a remote station 16. The cameras and monitors at both the robot and remote control stations allow for tele-conferencing between the patient and the person at the remote station(s). The robot 10 may be controlled by a number of different users. To accommodate for this the robot may have an arbitration system. The arbitration system may be integrated into the operating system of the robot 12. For example, the arbitration technique may be embedded into the operating system of the high-level controller 150.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The system 10 can be used for doctor proctoring where a doctor at the remote station provides instructions and feedback to a doctor located in the vicinity of the robot. For example, a doctor at the remote location can view a patient and assist a doctor at the patient location in a diagnosis. Likewise, the remote doctor can assist in the performance of a medical procedure at the robot location.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user<br>Notify requesting user that system is in use<br>Set timeout | Warn current user of pending user<br>Notify requesting user that system is in use<br>Set timeout = 5 m | Warn current user of pending user<br>Notify requesting user that system is in use<br>Set timeout = 5 m<br>Call back | Warn current user of pending user<br>Notify requesting user that system is in use<br>No timeout<br>Call back |
| | Caregiver | Warn current user of pending user.<br>Notify requesting user that system is in use.<br>Release control | Not Allowed | Warn current user of pending user<br>Notify requesting user that system is in use<br>Set timeout = 5 m<br>Queue or callback | Warn current user of pending user<br>Notify requesting user that system is in use<br>Set timeout = 5 m | Warn current user of pending user<br>Notify requesting user that system is in use<br>No timeout<br>Callback |
| | Doctor | Warn current user of pending user<br>Notify requesting user that system is in use<br>Release control | Warn current user of pending user<br>Notify requesting user that system is in use<br>Set timeout = 5 m | Warn current user of pending user<br>Notify requesting user that system is in use<br>No timeout<br>Callback | Notify requesting user that system is in use<br>No timeout<br>Queue or callback | Warn current user of pending user<br>Notify requesting user that system is in use<br>No timeout<br>Callback |
| | Family | Warn current user of pending user<br>Notify requesting user that system is in use<br>Release Control | Notify requesting user that system is in use<br>No timeout<br>Put in queue or callback | Warn current user of pending user<br>Notify requesting user that system is in use<br>Set timeout = 1 m | Warn current user of pending user<br>Notify requesting user that system is in use<br>Set timeout = 5 m<br>Queue or callback | Warn current user of pending user<br>Notify requesting user that system is in use<br>No timeout<br>Callback |
| | Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Command | Example | Description |
| --- | --- | --- |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., |

TABLE III-continued

Control Commands

| Command | Example | Description |
| --- | --- | --- |
| | | sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |
| print | print -doctor "<string>" -patient "<string>" -order "<string>" [-room "<string>"] [-id "<string>"] | The print command causes the robot printer to print accompanying information. |

Table IV provides a list of reporting commands that are generated by the robot and transmitted to the remote station through the network.

TABLE IV

Reporting Commands

| Command | Example | Description |
| --- | --- | --- |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. |

TABLE IV-continued

Reporting Commands

| Command | Example | Description |
|---|---|---|
| | | This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 154 of the robot high level controller 150 may operate a program that determines whether the robot 12 has received a robot control command within a time interval. For example, if the robot 12 does not receive a control command within 2 seconds then the processor 154 provides instructions to the low level controller 150 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

The robot may also have internal safety failure features. For example, the robot may monitor communication between the robot controller and the robot servo used to operate the platform motors. The robot monitor may switch a relay to terminate power to the platform motors if the monitor detects a lack of communication between the robot controller and the motor servo.

The remote station may also have a safety feature for the input device 32. For example, if there is no input from the joystick for a certain time interval (eg. 10 seconds) the computer 22 may not relay subsequent input unless the user presses a button for another time interval (eg. 2 seconds), which reactivates the input device.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A remote controlled robot system, comprising:
a remote control station that includes a station camera, a station monitor, a station microphone, and a station speaker; and,
a mobile robot located in a facility and capable of participating in a communication session with the remote control station, the mobile robot includes:
a mobile platform capable of maneuvering about a floor of the facility in response to movement commands received from the remote control station via a broadband network;
a robot monitor;
a first robot camera that faces substantially in the direction of the robot monitor;
a second robot camera that faces substantially in the direction of the floor;
a robot microphone; and,
a robot speaker,
wherein, during said communication session, the station monitor displays a display user interface that includes an image captured by the first robot camera in an upper portion of the display user interface and an image captured by the second robot camera in a lower portion of the display user interface, wherein a display area of the image from the first robot camera is larger than a display area of the image from the second robot camera, the robot monitor displays an image captured by the station camera, the station speaker reproduces a sound captured by the robot microphone, the robot speaker reproduces a sound captured by the station microphone, and the remote control station generates the movement commands in response to operation of an input device of the remote control station.

2. The system of claim 1, wherein the second robot camera is coupled to the mobile platform via a boom.

3. The system of claim 2, wherein said boom has at least one passive joint.

4. The system of claim 2, further comprising a head that includes the first robot camera and the robot monitor, and wherein said boom is connected to said head.

5. The system of claim 4, wherein said head moves in at least two degrees of freedom relative to the mobile platform.

6. The system of claim 1, wherein the display user interface simultaneously displays the images from the first and second robot cameras.

7. The system of claim 6, wherein the display user interface includes a graphical element that can be selected to change a display of the image captured by the second robot camera.

8. The system of claim 1, wherein the display user interface includes a robot view field, a station view field and an auxiliary camera view field.

9. The system of claim 8, wherein an image from said first robot camera is displayed in the robot view field.

10. The robot of claim 9, wherein an image from the second robot camera is displayed in the auxiliary view field.

11. The robot of claim 10, wherein the image captured by the station camera is displayed in the station view field.

12. A method for controlling a mobile robot in a facility using a remote control station, the method comprising:

establishing a communication session with the mobile robot via a broadband network, the robot having a mobile platform that can move about a floor of the facility;

transmitting movement commands from the remote control station to the mobile robot via a broadband network, the mobile robot including a robot monitor, a first robot camera that faces substantially in the direction of the robot monitor, a second robot camera that faces substantially in the direction of the floor, a robot microphone, and a robot speaker;

displaying, on a monitor of the remote station, a display user interface that includes an image captured by the first robot camera in an upper portion of the display user interface and an image captured by the second robot camera in a lower portion of the display user interface, wherein a display area of the image from the first robot camera is larger than a display area of the image from the second robot camera; and, transmitting an image captured by a camera of the remote station to the mobile robot for display on the robot monitor.

13. The method of claim 12, further comprising simultaneously displaying the images from the first and second robot cameras in the display user interface.

14. The method of claim 12, further comprising displaying the image from the station camera in the display user interface.

* * * * *